(12) United States Patent
Laffitte et al.

(10) Patent No.: US 11,040,940 B2
(45) Date of Patent: Jun. 22, 2021

(54) WEAKLY COLOURED SULFONIC ACID

(71) Applicant: ARKEMA FRANCE, Colombes (FR)

(72) Inventors: Jean-Alex Laffitte, Biarritz (FR); Bernard Monguillon, Nogent sur Marne (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/643,076

(22) PCT Filed: Aug. 30, 2018

(86) PCT No.: PCT/FR2018/052125
§ 371 (c)(1),
(2) Date: Feb. 28, 2020

(87) PCT Pub. No.: WO2019/043338
PCT Pub. Date: Mar. 7, 2019

(65) Prior Publication Data
US 2020/0181072 A1  Jun. 11, 2020

(30) Foreign Application Priority Data
Sep. 1, 2017 (FR) ...................... 1758098

(51) Int. Cl.
C07C 309/04 (2006.01)
C07C 309/35 (2006.01)
C07C 309/30 (2006.01)
C07C 309/06 (2006.01)
C07C 309/29 (2006.01)
C07C 303/42 (2006.01)
C23F 11/04 (2006.01)
C23F 11/18 (2006.01)

(52) U.S. Cl.
CPC .......... *C07C 309/04* (2013.01); *C07C 303/42* (2013.01); *C07C 309/06* (2013.01); *C07C 309/29* (2013.01); *C07C 309/30* (2013.01); *C07C 309/35* (2013.01); *C23F 11/04* (2013.01); *C23F 11/181* (2013.01)

(58) Field of Classification Search
None
See application file for complete search history.

(56) References Cited

U.S. PATENT DOCUMENTS

| 2,455,659 | A |   | 12/1948 | Duncan et al. |
| 2,534,201 | A |   | 12/1950 | Hutter |
| 3,505,367 | A | * | 4/1970 | Brunel .................. C07C 303/42 554/100 |
| 3,759,594 | A |   | 9/1973 | Cobb |
| 5,055,230 | A |   | 10/1991 | Clubley |
| 6,120,619 | A |   | 9/2000 | Goudiakas et al. |
| 6,329,073 | B1 |   | 12/2001 | Deruyck et al. |
| 2011/0108120 | A1 |   | 5/2011 | Fassbender et al. |
| 2017/0216550 | A1 |   | 8/2017 | Meyerhoff et al. |
| 2020/0347014 | A1 |   | 11/2020 | Laffitte et al. |

FOREIGN PATENT DOCUMENTS

| BE | 613 776 A | 8/1962 |
| EP | 0 931 854 A1 | 7/1999 |
| GB | 519823 | 4/1940 |
| WO | 89/04856 | 6/1989 |
| WO | 2006/086875 A1 | 8/2006 |

OTHER PUBLICATIONS

Lutropur® MSA (downloaded from https://biakhim.com.ua/index.php?option=com_k2&Itemid=1174&id=192_b53352be64a78cc571bb042a3ff93160&lang=ru&task=download&view=item on Aug. 6, 2020, first publicly available in 2013) (Year: 2013).*
CHSR ("Understanding Units of Measurement", downloaded from https://cfpub.epa.gov/ncer_abstracts/index.cfm/fuseaction/display.files/fileid/14285#:~:text=Parts%20per%20million%20and%20parts,equal%20to%206%2C000%20ug%2Fkg on Aug. 6, 2020 (Year: 2020).*
International Search Report for PCT/FR2018/052125, dated Nov. 21, 2018 (4 pages with English translation).
Written Opinion for PCT/FR2018/052125, dated Nov. 21, 2018 (5 pages).
Gaur, B., et al. Corrosion of metals and alloys in methane sulphonic acid. British Corrosion Journal. 1999. vol. 34, No. 1, pp. 63-66.
Final Office Action dated Apr. 15, 2021 received in U.S. Appl. No. 16/643,083 (12 pages).

* cited by examiner

*Primary Examiner* — Amy C Bonaparte
(74) *Attorney, Agent, or Firm* — Smith, Gambrell & Russell, LLP

(57) ABSTRACT

The subject of the present invention is a weakly corrosive and weakly coloured sulfonic acid, with an APHA colour index of less than 20, comprising chlorides and nitrites in a chloride/sulfonic acid molar ratio of between 1 ppm and 200 ppm, and a nitrite/sulfonic acid molar ratio of between 200 ppm and 6000 ppm, limits inclusive.

11 Claims, No Drawings

WEAKLY COLOURED SULFONIC ACID

The present invention relates to the field of sulfonic acids and more particularly the field of weakly coloured sulfonic acids, and also to the process for preparing same.

Sulfonic acids, and in particular sulfonic acids termed organic, such as for example methanesulfonic acid (MSA), para-toluenesulfonic acid (PTSA), benzenesulfonic acid (BS) or trifluoromethane sulfonic acid, are strong acids widely used in numerous applications, in particular in catalysis and in surface treatment, such as galvanoplasty, stripping, cleaning or descaling, to cite just the main examples, without being limited thereto.

However, it has been observed that aqueous solutions of such sulfonic acids corrode metals, the corrosion rates depending simultaneously on the acid concentration, on the temperature and on the nature of the metal. For example, at ambient temperature, stainless steel of 304L or 1.4307 type is corrodable at MSA concentrations greater than 5% by weight in water. Such corrosion risks are unacceptable in many applications, and particularly for the storage of these acids mainly when they are in aqueous solution.

In order to make sulfonic acids barely corrosive, or even non-corrosive, towards metals, and particularly towards stainless steels, numerous studies have already been carried out, among which one technique, which has shown satisfactory results, consists of the addition of nitrates to said acids. This method is in particular described by B. Gaur and H. S. Srinivasan ("*British Corrosion Journal*", 34(1), (1999), 63-66) who showed that the addition of ferric ions or nitrates makes it possible to produce an inhibitory effect on corrosion by MSA on various steels.

Other solutions have been studied, among which mention may for example be made of that described in application EP 0 931 854, which proposes inhibiting so the corrosion of stainless steels in organosulfonic acid medium, by adding at least one oxidizing agent chosen from salts or oxides of cerium(IV), of iron(III), of molybdenum(VI), of vanadium (V), nitrites and persulfates.

Sulfonic acids to which nitrites have been added are most especially advantageous owing to their quite particular nature of being not very corrosive with respect to metals and in particular stainless steels. These weakly corrosive (also termed "low-corrosion") acids unfortunately have the drawback of colouring more or less rapidly, depending on the nature of the sulfonic acid, of the nitrite used and of the nitrite concentration in said sulfonic acid.

This colouring can prove to be an impairment for the applications envisaged, in particular when the sulfonic acids are used as cleaning agents, as catalysts for reactions for producing products with high added value, and the like. In addition, the colouring can be considered to result from the presence of impurities which, in addition to the fact of polluting the sulfonic acid and making it unsuitable for the use envisaged, can at the very least make it incompatible with commercial specifications.

This colouring therefore represents a major drawback for "low-corrosion" sulfonic acids, that is to say for sulfonic acids which comprise nitrites to make them weakly corrosive with respect to metals and alloys which can be passivated, in particular based on iron, nickel, titanium, copper, aluminium, molybdenum, manganese, lead, and alloys thereof, and also pairs of these metals or alloys obtained by contact (crimping, riveting, bolting, welding, welding, brazing), in particular with respect to stainless steels, and in particular the common stainless steels (for example of AISI 304L and AISI 316L type), but also more generally any stainless steel as defined in the standard NF EN 10088-1.

The applicant has now discovered that the colouring of "low-corrosion" sulfonic acids is in particular due to the presence of chloride ions in said sulfonic acids.

In the present invention, it is considered that a sulfonic acid is "coloured" when its APHA colour is strictly greater than 20. Conversely, for the purposes of the present invention, a weakly coloured sulfonic acid is a sulfonic acid of which the APHA colour is less than 20, preferably less than 15, more particularly less than 10, most particularly less than 5.

The APHA colour is a colour standard named after the American Public Health Association and defined by the standard ASTM D1209, and more precisely ASTM D1209-05(2011). The APHA colour is a colour scale, sometimes also called "yellowing index", which makes it possible to evaluate the quality of the liquids which are pale to yellowish in colour. The APHA colour is measured using a colorimeter with a standard range of from 0 to 200 APHA.

In the present invention, the term "low-corrosion sulfonic acid" is intended to mean a sulfonic acid of which the potential remains virtually at the same level and does not rise back up after applying an amount of current of $-800$ $\mu A \cdot cm^{-2}$, for 1 minute, then stopping the application of this current, as explained below in the "low-corrosion" validation test protocol.

In other words, a low-corrosion sulfonic acid according to the present invention remains in the passive state after application of a current of $-800$ $\mu A \cdot cm^{-2}$, for 1 minute, whereas a sulfonic acid not in accordance with the present invention (corrosive) returns to the active state (corrosion) after depassivation by application of said amount of current of $-800$ $\mu A \cdot cm^{-2}$, for 1 minute.

The low-corrosion sulfonic acids of the present invention are conventional sulfonic acids to which at least one nitrite has been added, and the nitrite/sulfonic acid molar ratio of which is between 200 ppm and 6000 ppm, preferably between 400 ppm and 2000 ppm, in particular between 500 ppm and 1900 ppm.

In point of fact, conventional sulfonic acids can contain chloride ions in more or less significant amounts. The presence and the amount of chloride ions in conventional sulfonic acids can result from many factors, among which mention may, in a non-limiting manner, be made of the chlorinated derivative(s) used in the process for producing said conventional sulfonic acid itself, the chlorides or chlorinated derivatives present in the various solvents, additives, auxiliary substances, fillers intended to formulate said sulfonic acid in order to facilitate the processing thereof, the use thereof and the effectiveness thereof in the applications envisaged, and the like.

Without wanting to be bound by theory, it has been established that the presence of chloride ions leads to the colouring of sulfonic acids to which nitrite ions have been added in order to confer non-corrosive or weakly corrosive properties thereon.

It has now been discovered that it is possible to be able to provide a weakly coloured sulfonic acid, even when said acid comprises chloride ions, and nitrite ions added in order to confer non-corrosive or weakly corrosive properties thereon.

Thus, and according to a first aspect, the present invention relates to a sulfonic acid comprising:

a chloride/sulfonic acid molar ratio of between 1 ppm and 200 ppm, preferably between 5 ppm and 200 ppm, more preferably between 10 ppm and 200 ppm, more preferentially between 10 ppm and 190 ppm, limits inclusive, and a nitrite/sulfonic acid molar ratio of between 200 ppm and 6000 ppm, preferably between 400 ppm and 2000 ppm, particularly between 500 ppm and 1900 ppm, limits inclusive, and the APHA colour of which is less than 20, preferably less than 15, more particularly less than 10, most particularly less than 5.

In the present invention, the term "sulfonic acid" is intended to mean any sulfonic acid known to those skilled in the art and more particularly the sulfonic acids of formula R—SO$_3$H, where R represents a linear, branched or cyclic, saturated or unsaturated hydrocarbon-based chain comprising from 1 to 12 carbon atoms, which is unsubstituted or substituted with one or more radicals and/or atoms chosen from halogen (such as fluorine, chlorine or bromine) atoms, alkyl radicals containing from 1 to 6 carbon atoms and aryl and heteroaryl radicals comprising 6 or 10 ring members.

The term "alkyl" is intended to mean a linear or branched, saturated hydrocarbon-based radical. The term "aryl" is intended to mean an aromatic radical, preferably a phenyl or naphthyl radical, more preferentially a phenyl radical. The term "heteroaryl" is intended to mean an aromatic radical having one or more heteroatoms chosen from oxygen, nitrogen and sulfur.

Preferably, R represents a hydrocarbon-based chain comprising from 1 to 6 carbon atoms, more particularly chosen from methyl, ethyl, n-propyl, iso-propyl, n-butyl, iso-butyl, sec-butyl, tert-butyl, linear or branched pentyl radicals, linear or branched hexyl radicals, and phenyl and naphthyl radicals.

Thus, and in a non-limiting manner, the sulfonic acids included in the context of the present invention are preferably chosen from methanesulfonic acid, ethanesulfonic acid, n-propanesulfonic acid, iso-propanesulfonic acid, n-butanesulfonic acid, iso-butanesulfonic acid, sec-butanesulfonic acid, tert-butanesulfonic acid, trifluoromethanesulfonic acid, para-toluenesulfonic acid, benzenesulfonic acid, naphthalenesulfonic acid, and mixtures of two or more of them in any proportions.

According to one most particularly preferred embodiment, the sulfonic acid used in the context of the present invention is methanesulfonic acid, ethanesulfonic acid, trifluoromethanesulfonic acid or para-toluenesulfonic acid; entirely preferably, the sulfonic acid is methanesulfonic acid.

The sulfonic acid used in the context of the present invention may be sulfonic acid alone or as a mixture of two or more sulfonic acids, optionally in a solvented medium and optionally as a mixture with one or more additives and/or fillers well known to those skilled in the art.

Thus, the sulfonic acid(s) may be in solvented medium, said solvent possibly being water or an organic solvent or a mixture of organic solvents, or else water as a mixture with one or more other organic solvents. As a general rule, the concentration of sulfonic acid(s) in the solvent(s) is between 0.01% and 100%, limits inclusive, by weight of sulfonic acid(s) relative to the total weight of sulfonic acid(s) in solvented medium, it being understood that, when the concentration is equal to 100%, the amount of solvent is zero or negligible or undetectable. Preferably, this concentration is between 0.01% and 99.99%, preferably between 0.1% and 99.9%, more preferably between 0.5% and 75%, limits inclusive, by weight of sulfonic acid(s) relative to the total weight of sulfonic acid(s) in solvented medium.

The organic solvents indicated above and that can be used to solvent the sulfonic acid(s) may be of any type known to those skilled in the art, and preferably water-soluble organic solvents, such as alcohols, sulfoxides, mineral or organic acids, more preferentially methanol, ethanol, dimethyl sulfoxide, sulfuric acid, to cite just the most common ones and the most well-known ones among them.

The additives and fillers that may be present as a mixture with the sulfonic acids may for example be, in a non-limiting manner, one or more additives and/or fillers chosen from viscosity or rheology modifiers, foaming agents, anti-foams, surfactants, disinfectants, biocides, stabilizers, oxidizing agents, enzymes, pigments, dyes, fire retardants, flame retardants, fragrances, aromas, and the like.

These various additives and fillers are present in amounts well known to those skilled in the art, which can vary as a function of the effect desired, of the nature of the sulfonic acid used and of the application considered for said sulfonic acid used.

The addition of nitrite in the proportions previously indicated can be carried out according to any method known to those skilled in the art, in particular by adding one or more alkali metal or alkaline-earth metal nitrite(s), in solid form or in a form dissolved in a solvent, such as water. Such sulfonic acids with added nitrite are described for example in application EP 0 931 854.

The amount of chlorides present in the sulfonic acid can be easily controlled and adjusted according to the nature of the process for producing the sulfonic acid itself, and its degree of purity, which can be improved according to one or more of the techniques known to those skilled in the art, such as distillation, recrystallization, and the like.

In addition, the amount of chlorides present in the sulfonic acid can be easily controlled and adjusted according to the nature of the optional solvent(s), additive(s) and filler(s) which are added thereto. Those skilled in the art will easily understand that a sulfonic acid with a low chloride content will see this content increased if it is decided, for example, to dilute said sulfonic acid in water with a high concentration of chloride or else to add a filler such as a chloride-containing salt The low-corrosion sulfonic acid according to the present invention thus has an APHA colour of less than 20, preferably less than 15, more particularly less than 10, most particularly less than 5, that is to say an absence or virtual absence of colour, which makes it possible to have a low-corrosion sulfonic acid which thus corresponds to most or even all of the commercial specifications, in a very large number of application fields.

The present invention also concerns a composition comprising at least one sulfonic acid as defined above, a solvent as defined above, preferably water, and optionally one or more additive(s) and/or filler(s) as defined above.

The invention will be understood more clearly by means of the examples which follow, said examples not being in any way limiting, and serving solely to illustrate the invention.

EXAMPLES 135 g of methanesulfonic acid at 70% (that is to say diluted to 70% by weight in water) are introduced, with stirring (400 rpm) at 20° C., into a 250 ml three-necked round-bottomed flask. The solution obtained contains a chlorides/MSA molar ratio equal to 27 ppm.

Three different samples containing variable chlorides/MSA molar ratios are prepared from this methane sulfonic acid (MSA), already containing a chlorides/MSA ratio of 27 ppm. For this, solutions of chloride, in the form of 0.1 N hydrochloric acid, are then added to the starting methanesulfonic acid solution.

Four samples with variable chloride contents are thus obtained:
sample 1: chlorides/MSA molar ratio equal to 27 ppm (no chloride added)
sample 2: chlorides/MSA molar ratio equal to 66 ppm
sample 3: chlorides/MSA molar ratio equal to 100 ppm
sample 4: chlorides/MSA molar ratio equal to 220 ppm.

By means of an automatic pipette, 0.24 ml (i.e. 0.30375 g) of 40% (that is to say diluted to 40% by weight in water) $NaNO_2$ (i.e. 0.1215 g of pure $NaNO_2$) is then added, over the course of 1 min, to each sample. The $NaNO_2$/MSA molar ratio is 1800 ppm.

The round-bottomed flask is immediately hermetically closed and the whole is stirred (400 rpm) for 1 hour at 20° C. Nitrogen is then sparged into the solution (flow rate 10 ml·min$^{-1}$) for 360 min.

The colour of each sample is then measured using a LICO 620 colorimeter from the company Hach, with a standard range between 0 and 200 APHA. The device is pre-calibrated with standard solutions ranging from 0 to 200 APHA. A 4 ml sample of the solution of which it is desired to determine the colour is introduced into a cuvette supplied by Hach and the colour is read automatically on the device.

The results are collated in Table 1 below:

TABLE 1

| Sample tested | APHA colour |
|---|---|
| 1 | 2 |
| 2 | 7 |
| 3 | 12 |
| 4 | 23 |

It is considered that there is an absence of colouring when the APHA colour value measured is less than 20. Thus, it is noted that, for a chlorides/MSA ratio of less than or equal to 200 ppm, the MSA/inhibitor mixture is colourless, whereas for a chlorides/MSA ratio equal to 220 ppm, the APHA value is greater than 20 and the methanesulfonic acid is coloured.

There is therefore a correlation between the chloride content in a sulfonic acid containing a corrosion inhibitor, in nitrite form: the lower the chloride content, the less coloured the solution is, or the solution can even be considered to be colourless in many commercial specifications.

Measurement of Chlorides in a Sulfonic Acid:

The amount of chlorides present in a sulfonic acid is measured by argentometry using a potentiometer equipped with a silver sulfide electrode sold by the company Metrohm AG under the reference 6.0404.100.

Precisely 35 g of sulfonic acid are weighed into a beaker containing enough acetone to be able to immerse the electrode, and titration is carried out with a 0.005 N silver nitrate solution in acetic acid. The amount ($Q_{Cl}$) of chlorides (in ppm by weight) is expressed by the following formula:

$$Q_{Cl} = \frac{\text{Volume AgNO}_3 \text{(ml)} \times N \text{AgNO}_3 (m \text{ equivalent/mL}) \times 35\,500}{\text{weight of the sample (grams)}}$$

Measurement of the Nitrites in a Sulfonic Acid:

The nitrites can be quantitatively determined according to any method known to those skilled in the art and for example by ion chromatography.

The samples to be tested are diluted, approximately 150 times (0.6 g of sample then made up to 100 ml with ultrapure water), and passed over an ICS5000 instrument from the company Dionex™. The detection mode is conductimetry and the results are read relative to a pre-established calibration curve.

The calibration range is prepared from nitrite standards, and also from an MSA matrix. Solutions of the commercial nitrite standards (1000 mg·l$^{-1}$ in water, supplier CPA) are prepared at 1, 10 and 100 mg·l$^{-1}$ by diluting them in ultrapure water.

The MSA matrix is prepared from a commercial solution of MSA at 70% (Sigma-Aldrich) diluted in ultrapure water. To do this, 0.6 g of 70% MSA are weighed into a 100 ml volumetric flask, then the volume is made up with ultrapure water.

"Low-Corrosion" Validation Test Protocol

In order to verify the "low-corrosion" quality, within the meaning of the present invention, of a sulfonic acid, an electrochemical test is carried out using an assembly of 3 electrodes connected to a Biologic VMP3 potentiostat:
1) reference electrode: saturated calomel electrode or "SCE"
2) working electrode: test specimen of 304L stainless steel, 1 cm$^2$ in size, and
3) platinum counter electrode.

The test specimen of the material to be tested is polished with P400 abrasive paper then passivated for 1 hour in a 10% nitric acid solution at ambient temperature. This allows an identical starting state for all the tests. The temperature of the test is thermostatted at 20° C.±2° C.

The protocol applied comprises the following three steps:
a) monitoring of the rest potential of the working electrode (304L) in the sulfonic acid additivated according to the process of the present invention, that is to say measurement of the potential of the material in the solution as a function of time, for 30 minutes,
b) immersion of the three-electrode system in a standard (i.e. non-additivated) sulfonic acid solution, then application to the working electrode of a current of −800 µA·cm$^{-2}$ for 1 minute in order to depassivate the material artificially by fixing the potential thereof in the corrosion range,
c) immersion of the three-electrode system again in the sulfonic acid solution additivated according to the process of the present invention, and monitoring again of the rest potential of the working electrode, until stabilization thereof.

Results of the Validation Test

In the case of a standard, that is to say non-additivated, methanesulfonic acid in solution at 70% by weight in water, after application of an amount of current of −800 µA·cm$^{-2}$, the potential of the working electrode (test specimen of 304L stainless steel) drops to around −350 mV, which corresponds to the passing of the 304L stainless steel into the active state. When the application of the current is stopped, the potential of the material remains virtually at the same level and does not rise back up. The 304L stainless steel remains in the active state and corrodes.

The behaviour is completely different in a solution at 70% by weight in water of a nitrite-additivated methanesulfonic acid.

A rest potential of the 304L stainless steel of about 750 mV after 30 minutes is first of all noted. During the application of the current of −800 µA·cm$^{-2}$, the potential of the material drops to around −200 mV (passing of the 304L stainless steel into the active state). When the application of the current is stopped, the potential of the material rises back up very rapidly. It is 780 mV after 2 hours of monitoring the potential and a total absence of corrosion is noted.

In all cases (samples 1, 2, 3 and 4 above), the sodium nitrite-additivated methanesulfonic acid is a low-corrosion methanesulfonic acid within the meaning of the present invention.

The invention claimed is:

1. Sulfonic acid comprising:
a chloride/sulfonic acid molar ratio of between 1 ppm and 200 ppm, limits inclusive, and
a nitrite/sulfonic acid molar ratio of between 200 ppm and 6000 ppm, limits inclusive, and the APHA colour of which is less than 20.

2. The sulfonic acid according to claim 1, having the formula R—SO$_3$H, where R is selected from linear, branched or cyclic hydrocarbons having from 1 to 12 carbon atoms, where the hydrocarbons are unsubstituted or substituted with one or more radicals and/or atoms selected from halogen atoms, alkyl radicals containing from 1 to 6 carbon atoms, aryl or heteroaryl radicals having 6 or 10 ring members.

3. The sulfonic acid according to claim 1, selected from methanesulfonic acid, ethanesulfonic acid, n-propanesulfonic acid, iso-propanesulfonic acid, n-butanesulfonic acid, iso-butanesulfonic acid, sec-butanesulfonic acid, tert-butanesulfonic acid, trifluoromethanesulfonic acid, para-toluenesulfonic acid, benzenesulfonic acid, naphthalenesulfonic acid, or mixtures thereof.

4. The sulfonic acid according to claim 1, selected from the group consisting of methanesulfonic acid, ethanesulfonic acid, trifluoromethanesulfonic acid and para-toluenesulfonic acid.

5. Composition comprising at least one sulfonic acid according to claim 1, and a solvent, where said solvent is water, an organic solvent a mixture of organic solvents, or water as a mixture with one or more organic solvents.

6. Composition comprising at least one sulfonic acid according to claim 1, and one or more additives and/or fillers selected from viscosity or rheology modifiers, foaming agents, anti-foams, surfactants, disinfectants, biocides, stabilizers, oxidizing agents, enzymes, pigments, dyes, fire retardants, flame retardants, fragrances and aromas.

7. Composition comprising at least one sulfonic acid according to claim 1, a solvent, and optionally one or more additive(s) and/or filler(s).

8. The sulfonic acid according to claim 1, where the sulfonic acid is methanesulfonic acid.

9. The sulfonic acid according to claim 1, where the chloride/sulfonic acid molar ratio is between 5 ppm and 200 ppm, limits inclusive, and the nitrite/sulfonic acid molar ratio is of between 400 ppm and 2000 ppm, limits inclusive, and the APHA colour of which is less than 15.

10. The sulfonic acid according to claim 1, where the chloride/sulfonic acid molar ratio is between 10 ppm and 200 ppm, limits inclusive, and the nitrite/sulfonic acid molar ratio is between 400 ppm and 2000 ppm, limits inclusive, and the APHA colour of which is less than 10.

11. The sulfonic acid according to claim 1, where the chloride/sulfonic acid molar ratio is between 10 ppm and 190 ppm, limits inclusive, and the nitrite/sulfonic ratio is between 500 ppm and 1900 ppm, limits inclusive, and the APHA colour is less than 5.

* * * * *